US010001821B2

(12) United States Patent
Dehaan et al.

(10) Patent No.: US 10,001,821 B2
(45) Date of Patent: *Jun. 19, 2018

(54) CLOUD MANAGEMENT WITH POWER MANAGEMENT SUPPORT

(71) Applicant: Red Hat, Inc., Raleigh, NC (US)

(72) Inventors: Michael Paul Dehaan, Morrisville, NC (US); Scott Jared Henson, Raleigh, NC (US); John Joseph Eckersberg, II, Apex, NC (US)

(73) Assignee: Red Hat, Inc., Raleigh, NC (US)

( * ) Notice: Subject to any disclaimer, the term of this patent is extended or adjusted under 35 U.S.C. 154(b) by 261 days.

This patent is subject to a terminal disclaimer.

(21) Appl. No.: 14/822,742

(22) Filed: Aug. 10, 2015

(65) Prior Publication Data

US 2015/0346787 A1 Dec. 3, 2015

Related U.S. Application Data

(63) Continuation of application No. 12/473,987, filed on May 28, 2009, now Pat. No. 9,104,407.

(51) Int. Cl.

| *G06F 15/16* | (2006.01) |
|---|---|
| *G06F 1/26* | (2006.01) |
| *H04L 12/24* | (2006.01) |
| *G06F 9/455* | (2018.01) |
| *G06F 1/32* | (2006.01) |
| *G06F 9/50* | (2006.01) |

(52) U.S. Cl.
CPC .............. *G06F 1/26* (2013.01); *G06F 1/3203* (2013.01); *G06F 9/45558* (2013.01); *G06F 9/5072* (2013.01); *G06F 9/5094* (2013.01); *H04L 41/0806* (2013.01); *H04L 41/0823* (2013.01); *G06F 2009/45575* (2013.01); *G06F 2009/45595* (2013.01); *Y02B 60/142* (2013.01)

(58) Field of Classification Search
CPC ................... G06F 1/26; G06F 1/3203; G06F 2009/45575; G06F 9/45558; G06F 9/5077; G06F 9/5094; H04L 41/0806; H04L 41/0823; Y02B 60/142
See application file for complete search history.

(56) References Cited

U.S. PATENT DOCUMENTS

| 6,463,457 B1 | 10/2002 | Armentrout et al. |
|---|---|---|
| 7,313,796 B2 | 12/2007 | Hamilton et al. |
| 7,439,937 B2 | 10/2008 | Ben-Shachar et al. |
| 7,529,785 B1 | 5/2009 | Spertus et al. |
| 7,546,462 B2 | 6/2009 | Upton |

(Continued)

OTHER PUBLICATIONS

Morgan, "Systems and Methods for Detecting Resource Consumption Events Over Sliding Intervals in Cloud-Based Network", U.S. Appl. No. 13/149,235, filed May 31, 2011.

(Continued)

*Primary Examiner* — David R Lazaro
(74) *Attorney, Agent, or Firm* — Lowenstein Sandler LLP

(57) ABSTRACT

A system and method for managing power in virtualized computer systems are disclosed. In accordance with one embodiment, a request to instantiate a virtual machine is received. A processor determines that a power state is to be altered to instantiate the virtual machine on a computing system, and in response to the determination, alters the power state.

20 Claims, 4 Drawing Sheets

(56) References Cited

U.S. PATENT DOCUMENTS

| | | |
|---|---|---|
| 7,596,620 B1 | 9/2009 | Colton et al. |
| 2001/0039497 A1 | 11/2001 | Hubbard |
| 2002/0069276 A1 | 6/2002 | Hino et al. |
| 2002/0165819 A1 | 11/2002 | McKnight et al. |
| 2003/0037258 A1 | 2/2003 | Koren |
| 2003/0110252 A1 | 6/2003 | Yang-Huffman |
| 2003/0135609 A1 | 7/2003 | Carlson et al. |
| 2004/0162902 A1 | 8/2004 | Davis |
| 2004/0210591 A1 | 10/2004 | Hirschfeld et al. |
| 2004/0210627 A1 | 10/2004 | Kroening |
| 2004/0268347 A1 | 12/2004 | Knauerhase et al. |
| 2005/0131898 A1 | 6/2005 | Fatula |
| 2005/0144060 A1 | 6/2005 | Chen et al. |
| 2005/0182727 A1 | 8/2005 | Robert et al. |
| 2005/0289540 A1 | 12/2005 | Nguyen et al. |
| 2006/0075042 A1 | 4/2006 | Wang et al. |
| 2006/0085530 A1 | 4/2006 | Garrett |
| 2006/0085824 A1 | 4/2006 | Bruck et al. |
| 2006/0130144 A1 | 6/2006 | Wernicke |
| 2006/0177058 A1 | 8/2006 | Sarwono et al. |
| 2006/0224436 A1 | 10/2006 | Matsumoto et al. |
| 2007/0011291 A1 | 1/2007 | Mi et al. |
| 2007/0028001 A1 | 2/2007 | Phillips et al. |
| 2007/0226715 A1 | 9/2007 | Kimura et al. |
| 2007/0260723 A1* | 11/2007 | Cohen .................. G06F 9/5027 709/223 |
| 2007/0283282 A1 | 12/2007 | Bonfigllo et al. |
| 2007/0294676 A1 | 12/2007 | Mellor et al. |
| 2008/0080396 A1 | 4/2008 | Meijer et al. |
| 2008/0080718 A1 | 4/2008 | Meijer et al. |
| 2008/0082538 A1 | 4/2008 | Meijer et al. |
| 2008/0082601 A1 | 4/2008 | Meijer et al. |
| 2008/0083025 A1 | 4/2008 | Meijer et al. |
| 2008/0083040 A1 | 4/2008 | Dani et al. |
| 2008/0086727 A1 | 4/2008 | Lam et al. |
| 2008/0091613 A1 | 4/2008 | Gates et al. |
| 2008/0104608 A1 | 5/2008 | Hyser et al. |
| 2008/0215796 A1 | 9/2008 | Lam et al. |
| 2008/0240150 A1 | 10/2008 | Dias et al. |
| 2009/0012885 A1 | 1/2009 | Cahn |
| 2009/0025006 A1 | 1/2009 | Waldspurger |
| 2009/0037496 A1 | 2/2009 | Chong et al. |
| 2009/0089078 A1 | 4/2009 | Bursey |
| 2009/0099940 A1 | 4/2009 | Frederick et al. |
| 2009/0132695 A1 | 5/2009 | Surtani et al. |
| 2009/0177514 A1 | 7/2009 | Hudis et al. |
| 2009/0210527 A1 | 8/2009 | Kawato |
| 2009/0210875 A1 | 8/2009 | Bolles et al. |
| 2009/0217267 A1 | 8/2009 | Gebhart et al. |
| 2009/0222805 A1 | 9/2009 | Faus et al. |
| 2009/0228950 A1 | 9/2009 | Reed et al. |
| 2009/0248693 A1 | 10/2009 | Sagar et al. |
| 2009/0249287 A1 | 10/2009 | Patrick |
| 2009/0260007 A1 | 10/2009 | Beaty et al. |
| 2009/0265707 A1 | 10/2009 | Goodman et al. |
| 2009/0271324 A1 | 10/2009 | Jandhyala et al. |
| 2009/0276771 A1 | 11/2009 | Nickolov et al. |
| 2009/0287691 A1 | 11/2009 | Sundaresan et al. |
| 2009/0293056 A1 | 11/2009 | Ferris |
| 2009/0299905 A1 | 12/2009 | Mestha et al. |
| 2009/0299920 A1 | 12/2009 | Ferris et al. |
| 2009/0300057 A1 | 12/2009 | Friedman |
| 2009/0300149 A1 | 12/2009 | Ferris et al. |
| 2009/0300151 A1 | 12/2009 | Friedman et al. |
| 2009/0300152 A1 | 12/2009 | Ferris |
| 2009/0300169 A1 | 12/2009 | Sagar et al. |
| 2009/0300210 A1 | 12/2009 | Ferris |
| 2009/0300423 A1 | 12/2009 | Ferris |
| 2009/0300607 A1 | 12/2009 | Ferris et al. |
| 2009/0300608 A1 | 12/2009 | Ferris |
| 2009/0300635 A1 | 12/2009 | Ferris |
| 2009/0300641 A1 | 12/2009 | Friedman et al. |
| 2009/0300719 A1 | 12/2009 | Ferris |
| 2010/0042720 A1 | 2/2010 | Stienhans et al. |
| 2010/0050172 A1 | 2/2010 | Ferris |
| 2010/0057831 A1 | 3/2010 | Williamson |
| 2010/0058347 A1 | 3/2010 | Smith et al. |
| 2010/0131324 A1 | 5/2010 | Ferris |
| 2010/0131590 A1 | 5/2010 | Coleman et al. |
| 2010/0131624 A1 | 5/2010 | Ferris |
| 2010/0131649 A1 | 5/2010 | Ferris |
| 2010/0131948 A1 | 5/2010 | Ferris |
| 2010/0131949 A1 | 5/2010 | Ferris |
| 2010/0132016 A1 | 5/2010 | Ferris |
| 2010/0169477 A1 | 7/2010 | Stienhans et al. |
| 2010/0220622 A1 | 9/2010 | Wei |
| 2010/0029936 A1 | 11/2010 | Stienhans et al. |
| 2010/0299366 A1 | 11/2010 | Stienhans et al. |
| 2010/0306337 A1* | 12/2010 | DeHaan .................. G06F 8/63 709/213 |
| 2011/0016214 A1 | 1/2011 | Jackson |
| 2011/0022812 A1* | 1/2011 | van der Linden .... G06F 9/5077 711/163 |
| 2011/0131335 A1 | 6/2011 | Spaltro et al. |

OTHER PUBLICATIONS

Morgan, "Systems and Methods for Triggering Workload Movement Based on Policy Stack Having Multiple Slectable Inputs", U.S. Appl. No. 13/149,418, filed May 31, 2011.

Morgan, "Systems and Methods for Cloud Deployment Engine for Selective Workload Migration or Federation Based on Workload Conditions", U.S. Appl. No. 13/117,937, filed May 27, 2011.

Morgan, "Systems and Methods for Tracking Cloud Installation Information Using Cloud-Aware Kernel of Operating System", U.S. Appl. No. 13/149,750, filed May 31, 2011.

Morgan, "System and Methods for Introspective Application Reporting to Facilitate Virtual Machine Movement Between Cloud Hosts", U.S. Appl. No. 13/118,009, filed May 27, 2011.

Morgan, "System and Methods for Self-Moving Operating System Installation in Cloud-Based Network", U.S. Appl. No. 13/149,877, filed May 31, 2011.

Morgan, "Systems and Methods for Generating Optimized Resource Consumption Periods for Multiple Users on Combined Basis", U.S. Appl. No. 13/037,359, filed Mar. 1, 2011.

Morgan, "Systems and Methods for Metering Cloud Resource Consumption Using Multiple Hierarchical Subscription Periods", U.S. Appl. No. 13/037,360, filed Mar. 1, 2011.

Morgan, "Systems and Methods for Generating Marketplace Brokerage Exchange of Excess Subscribed Resources Using Dynamic Subscription Periods", U.S. Appl. No. 13/037,351, filed Feb. 28, 2011.

DeHaan et al., "Systems and Methods for Remote Management of Networked Systems Using Secure Modular Platform", U.S. Appl. No. 12/130,424, filed May 30, 2008.

"RBuilder and the rPath Appliance Platform", 2007 rPath, Inc., www.rpath.com, 3 pages.

Healey, "Virtualizing Support", Mar. 2008 White Paper, www.idc.com, 9 pages.

White Paper, "Best Practices for Building Virtual Appliances", 2008 rPath, Inc., www.rpath.com, 6 pages.

DeHaan, "Methods and Systems for Abstracting Cloud Management", U.S. Appl. No. 12/474,113, filed May 28, 2009.

Ferris, "Methods and Systems for Providing a Market for User-Controlled Resources to be Provided to a Cloud Computing Environment", U.S. Appl. No. 12/390,617, filed Feb. 23, 2009.

Ferris, "Methods and Systems for Communicationg with Third Party Resources in a Cloud Computing Environment", U.S. Appl. No. 12/390,598, filed Feb. 23, 2009.

Ferris, "Systems and Methods for Extending Sercurity Platforms to Cloud-Based Networks", U.S. Appl. No. 12/391,802, filed Feb. 24, 2009.

DeHaan, "Methods and Systems for Flexible Cloud Management", U.S. Appl. No. 12/473,041, filed May 27, 2009.

DeHaan, "Systems and Methods for Power Management in Managed Network Having Hardware-Based and Virtual Resources", U.S. Appl. No. 12/475,448, filed May 29, 2009.

(56) References Cited

OTHER PUBLICATIONS

Ferris, "Methods and Systems for Providing a Universal Marketplace for Resources for Delilvery to a Cloud Computing Environment", U.S. Appl. No. 12/475,228, filed May 29, 2009.
DeHaan, "Methods and Systems for Automated Scaling of Cloud Computing Systems", U.S. Appl. No. 12/474,707, filed May 29, 2009.
DeHaan, "Methods and Systems for Securely Terminating Processes in a Cloud Computing Environment", U.S. Appl. No. 12/550,157, filed Aug. 28, 2009.
DeHaan, "Methods and Systems for Flexible Cloud Management Including External Clouds", U.S. Appl. No. 12/551,506, filed Aug. 31, 2009.
DeHaan, "Methods and Systems for Abstracting Cloud Management to Allow Communication Between Independently Cotnrolled Clouds", U.S. Appl. No. 12/551,096, filed Aug. 31, 2009.
DeHaan, "Methods and Systems for Automated Migration of Cloud Processes to External Clouds", U.S. Appl. No. 12/551,459, filed Aug. 31, 2009.
Ferris, "Methods and Systems for Pricing Software Infrastructure for a Cloud Computing Environment", U.S. Appl. No. 12/551,517, filed Aug. 31, 2009.
Ferris et al., "Metering Software Infrastructure in a Cloud Computing Environment", U.S. Appl. No. 12/551,514, filed Aug. 31, 2009.
DeHaan, "Systems and Methods for Sercure Distributed Storage", U.S. Appl. No. 12/610,081, filed Oct. 30, 2009.
Ferris et al., "Methods and Systems for Monitoring Cloud Computing Environment", U.S. Appl. No. 12/627,764, filed Nov. 30, 2009.
Ferris et al., "Methods and Systems for Detecting Events in Cloud Computing Environment and Performing Actions Upon Occurrence of the Events", U.S. Appl. No. 12/627,646, filed Nov. 30, 2009.
Ferris et al., "Methods and Systems for Verifying Software License Compliance in Cloud Computing Environment", U.S. Appl. No. 12/627,643, filed Nov. 30, 2009.
Ferris et al., "Systems and Methods for Service Aggregation Using Graduated Service Levels in a Cloud Network", U.S. Appl. No. 12/628,112, filed Nov. 30, 2009.
Ferris, "Methods and Systems for Genereating a Software License Knowledge Base for Verifying Software License Compliance in Cloud Computing Environment", U.S. Appl. No. 12/628,156, filed Nov. 30, 2009.
Ferris et al., "Methods and Systems for Converting Standard Licenses for Use in Cloud Computing Environments", U.S. Appl. No. 12/714,099, filed Feb. 26, 2010.
Ferris et al., "Systems and Methods for Managing a Software Subscription in a Cloud Network", U.S. Appl. No. 12/714,096, filed Feb. 26, 2010.
Ferris et al., "Methods and Systems for Providing Deployment Architectures in Cloud Computing Environments", U.S. Appl. No. 12/714,427, filed Feb. 26, 2010.
Ferris et al., "Methods and Systems for Matching Resource with Cloud Computing Environment", U.S. Appl. No. 12/714,113, filed Feb. 26, 2010.
Ferris et al., "Systems and Methods for Generating Cross-Cloud Computing Appliances", U.S. Appl. No. 12/714,315, filed Feb. 26, 2010.
Ferris et al., "Systems and Methods for Cloud-Based Brokerage Exchange of Software Entitlements", U.S. Appl. No. 12/714,302, filed Feb. 26, 2010.
Ferris et al., "Methods and Systems for Offering Additional License Terms During Conversion of Standard Software Licenses for Use in Cloud Computing Environments", U.S. Appl. No. 12/714,065, filed Feb. 26, 2010.
Ferris et al., "Systems and Methods for a Usage Manager for Cross-Cloud Appliances", U.S. Appl. No. 12/714,334, filed Feb. 26, 2010.

Ferris et al., "Systems and Methods for Delivery of User-Controlled Resources in Cloud Environments Via a Resource Specification Language Wrapper", U.S. Appl. No. 12/790,294, filed May 28, 2010.
Ferris et al., "Systems and Methods for Managing Multi-Level Service Level Agreements in Cloud-Based Networks", U.S. Appl. No. 12/789,660, filed May 28, 2010.
Ferris et al., "Methods and Systems for Generating Cross-Mapping of Vendor Software in a Cloud Computing Environment", U.S. Appl. No. 12/790,527, filed May 28, 2010.
Ferris et al., "Methods and Systems for Cloud Deployment Analysis Featuring Relative Cloud Resource Importance", U.S. Appl. No. 12/790,366, filed May 28, 2010.
Ferris et al., "Systems and Methods for Generating Customized Build Options for Cloud Deployment Matching Usage Profile Against Cloud Infrastructure Options", U.S. Appl. No. 12/789,701, filed May 28, 2010.
Ferris et al., "Systems and Methods for Exporting Usage History Data as Input to a Management Platform of a Target Cloud-Based Network", U.S. Appl. No. 12/790,415, filed May 28, 2010.
Ferris et al., "Systems and Methods for Cross-Vendor Mapping Service in Cloud Networks", U.S. Appl. No. 12/790,162, filed May 28, 2010.
Ferris et al., "Systems and Methods for Cross-Cloud Vendor Mapping Service in a Dynamic Cloud Marketplace", U.S. Appl. No. 12/790,229, filed May 28, 2010.
Ferris et al., "Systems and Methods for Aggregate Monitoring of Utilization Data for Vendor Products in Cloud Networks", U.S. Appl. No. 12/790,039, filed May 28, 2010.
Ferris, et al., "Cominatorial Optimization of Multiple Resources Across a Set of Cloud-Based Networks", U.S. Appl. No. 12/953,718, filed Nov. 24, 2010.
Ferris et al., "Systems and Methods for Matching a Usage History to a New Cloud", U.S. Appl. No. 12/953,757, filed Nov. 24, 2010.
Ferris et al., "Systems and Methods for Identifying Usage Histories for Producing Optimized Cloud Utilization", U.S. Appl. No. 12/952,930, filed Nov. 23, 2010.
Ferris et al., "Systems and Methods for Identifying Service Dependencies in a Cloud Deployment", U.S. Appl. No. 12/952,857, filed Nov. 23, 2010.
Ferris et al., "Systems and Methods for Migrating Subscribed Services in a Cloud Deployment", U.S. Appl. No. 12/955,277, filed Nov. 29, 2010.
Ferris et al., "Systems and Methods for Migrating Subscribed Services from a Set of Clouds to a Second Set of Clouds", U.S. Appl. No. 12/957,281, filed Nov. 30.
Morgan, "Systems and Methods for Generating Multi-Cloud Incremental Billing Capture and Administration", U.S. Appl. No. 12/954,323, filed Nov. 24, 2010.
Morgan, "Systems and Methods for Aggregating Marginal Subscription Offsets in a Set of Multiple Host Clouds", U.S. Appl. No. 12/954,400, filed Nov. 24, 2010.
Morgan, "Generating Dynamically Configurable Subscription Parameters for Temporary Migration of Predictive User Workloads in Cloud Network", U.S. Appl. No. 12/954,378, filed Nov. 24, 2010.
Morgan, "Managing Subscribed Resource Limits in Cloud Network Using Variable or Instantaneous Consumption Tracking Periods", U.S. Appl. No. 12/954,352, filed Nov. 24, 2010.
Ferris et al., "Systems and Methods for Migrating Software Modules into One or More Clouds", U.S. Appl. No. 12/952,701, filed Nov. 23, 2010.
Ferris et al., "Brokering Optimized Resource Supply Costs in Host Cloud-Based Network Using Predictive Workloads", U.S. Appl. No. 12/957,274, filed Nov. 30, 2010.
Ferris et al., "Reclassifying Virtual Machines to Target Virtual Machines or Appliances Based on Code Analysis in a Cloud Environment", U.S. Appl. No. 12/957,267, filed Nov. 30, 2010.

\* cited by examiner

CLOUD MANAGEMENT WITH POWER MANAGEMENT SUPPORT

CROSS-REFERENCE TO RELATED APPLICATIONS

This application is a continuation of U.S. patent application Ser. No. 12/473,987, filed May 28, 2009, and hereby incorporated by reference.

FIELD

This invention relates generally to network computing, more particularly, to systems and methods for cloud computing related networks, services and products.

DESCRIPTION OF THE RELATED ART

The advent of cloud-based computing architectures has opened new possibilities for the rapid and scalable deployment of virtual Web stores, media outlets, and other on-line sites or services. In general, a cloud-based architecture deploys a set of hosted resources such as processors, operating systems, software and other components that can be combined or strung together to form virtual machines. A user or customer can request the instantiation of a virtual machine or set of machines from those resources from a central server or management system to perform intended tasks or applications. For example, a user may wish to set up and instantiate a virtual server from the cloud to create a storefront to market products or services on a temporary basis, for instance, to sell tickets to an upcoming sports or musical performance. The user can lease or subscribe to the set of resources needed to build and run the set of instantiated virtual machines on a comparatively short-term basis, such as hours or days, for their intended application.

Currently, cloud-based computing architectures are supported by dedicated servers used solely to operate the clouds. These dedicated servers utilize unitary virtualization schemes in order to instantiate virtual machines in the cloud. Likewise, these architectures lack flexibility in selecting resources to include in the cloud. Moreover, the dedicated servers may require direct interaction from an administrator to invoke virtual machines on the dedicated servers.

BRIEF DESCRIPTION OF THE DRAWINGS

Various features of the embodiments can be more fully appreciated, as the same become better understood with reference to the following detailed description of the embodiments when considered in connection with the accompanying figures, in which.

DETAILED DESCRIPTION OF EMBODIMENTS

Figure 1:
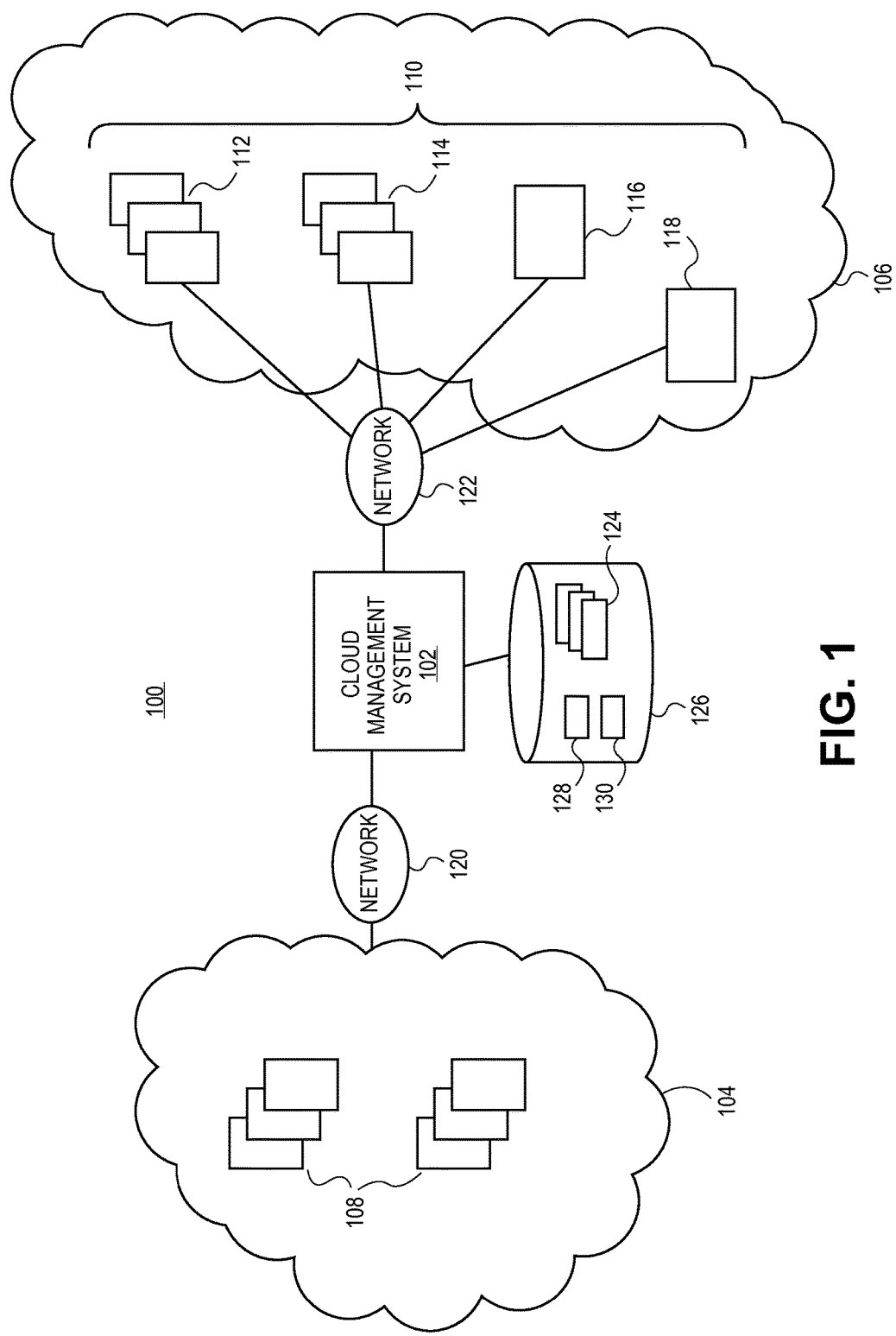
FIG. 1 illustrates an exemplary cloud computing architecture in which various embodiments of the present teachings can be practiced.

For simplicity and illustrative purposes, the principles of the present teachings are described by referring mainly to exemplary embodiments thereof. However, one of ordinary skill in the art would readily recognize that the same principles are equally applicable to, and can be implemented in, all types of information and systems, and that any such variations do not depart from the true spirit and scope of the present teachings. Moreover, in the following detailed description, references are made to the accompanying figures, which illustrate specific embodiments. Electrical, mechanical, logical and structural changes may be made to the embodiments without departing from the spirit and scope of the present teachings. The following detailed description is, therefore, not to be taken in a limiting sense and the scope of the present teachings is defined by the appended claims and their equivalents.

Embodiments of the present teachings relate to systems and methods for flexible management of a cloud computing environment. More particularly, embodiments relate to platforms and techniques in which a cloud management system can identify and utilize computing resources for instantiating virtual machines in a cloud including managing the power systems of the computing resources to instantiate the virtual machines.

According to embodiments, the cloud management system can be configured to identify and manage computing systems, and to identify the power management systems of the computing systems and control the power management of the computing systems during the installation of virtual machines. The cloud management system can be utilized in any type of cloud architecture regardless of the type of computing systems, the power management systems utilized by the computing systems, and the virtualization scheme used to instantiate the virtual machines. For example, the cloud management system can be used in dedicated cloud environments. Likewise, the cloud management system can be utilized in existing data centers in order to support ad-hoc clouds formed from existing and available computing resources.

According to embodiments, the cloud management system can be configured to identify the computing system and computing resources available to support the cloud. Additionally, the cloud management system can be configured to identify power management systems controlling the power provided to the computing systems. The cloud management system can be configured to maintain an inventory of computing systems including the computing resources available to the cloud, the current utilization of those resources, and the identification of any power management systems supporting the computing systems.

According to embodiments, when a requester requests use of the cloud, the cloud management system can be configured to receive specifications of the cloud usage from the requester. The specifications can include how the requester plans to use the cloud (mail server, application server, web server, etc.) and/or specific requirements for the computing resources (amount of processing power, amount of memory, amount of storage, amount of bandwidth, etc.). The cloud management system can be configured to utilize the specifications from the requester and the inventory of available computing resources to determine which cloud resources to devote to the requester's virtual machines to maximize the computing resources and meet the requester's specifications.

According to embodiments, when determining the computing systems and computing resources with which to support the virtual machines, the cloud management system can be configured to determine if the operational state of the virtual machines and/or the computing systems needs to be altered in order to instantiate the virtual machines. If the operational state of the computing systems needs to be altered, the cloud management system can be configured to retrieve the identification of the power management systems supporting the computing systems. The cloud management system can be configured to utilize the identification of the power management systems to instruct the power management systems to alter the power state of the computing system in order to instantiate the virtual machines.

By supporting a cloud regardless of the infrastructure and virtualization scheme, the cloud management system can create, manage, and support the cloud on any type of computing resources. Additionally, by maintaining and interacting the with power management systems of the computing systems, the cloud management system can instantiate the virtual machines without interacting directly with the computer systems or requiring action by other parties to alter the power state of the computing systems in order to instantiate the virtual machines. As such, the cloud management system can provide flexibility and efficiency to any cloud computing environment.

FIG. 1 illustrates an overall cloud computing environment 100, in which systems and methods for the flexible management of the cloud computing environment 100, according to embodiments of the present teachings. According to embodiments, a cloud management system 102 can be configured to mange one or more clouds, such as a dedicated cloud 104 and an ad-hoc cloud 106. As used herein, a "cloud" can comprise a collection of computing resources that can be invoked to instantiate a virtual machine, process, or other resource for a limited or defined duration.

As shown for example in FIG. 1, the collection of computing resources supporting the dedicated cloud 104 can comprise a set of resource servers 108 configured to deliver computing resources and components needed to instantiate a virtual machine, process, or other resource. For example, one group of resource servers can host and serve an operating system or components thereof to deliver to and instantiate a virtual machine. Another group of resource servers can accept requests to host computing cycles or processor time, to supply a defined level of processing power for a virtual machine. A further group of resource servers can host and serve applications to load on an instantiation of a virtual machine, such as an email client, a browser application, a messaging application, or other applications or software. Other types of resource servers are possible.

In embodiments, in addition to supporting the dedicated cloud 104, the cloud management system 102 can be configured to support the ad-hoc cloud 106. The ad-hoc cloud 106 can be composed of a variety of computing resources that may not be dedicated to a cloud but can have available computing resources to contribute to the ad-hoc cloud 106. For example, a corporation or university can have a large number of computing resources that support a variety of process (email, websites, individual user computing, and the like). The corporation or university can utilize the available excess computing resources to support an ad-hoc cloud, such as ad-hoc cloud 106.

In embodiments, as shown in FIG. 1, the ad-hoc cloud 106 can be supported by a number of computing systems 110. For example, the computing systems 110 can include a variety of systems such as a set of servers 112 and 114 and standalone user computing systems 116 and 118. The computing systems 110 can include hardware resources, such as processors, memory, network hardware, storage devices, and the like, and software resources, such as operating systems (OS), application programs, and the like.

In embodiments, the entire set of resource servers 108 or other hardware or software resources used to support the cloud 104 and the computing systems 110 used to support the ad-hoc cloud 106 can be managed by the cloud management system 102. The cloud management system 102 can comprise a dedicated or centralized server and/or other software, hardware, and network tools that communicate via one or more networks 120 and networks 122, such as the Internet or other public or private network, with all sets of resource servers 108 to manage the cloud 104 and with computing systems 110 to manage the ad-hoc cloud 106 and their operation.

In embodiments, to manage the clouds 104 and 106, the cloud management system 102 can be configured identify the computing resources of the set of resource servers 108 and computing systems 110. The cloud management system 102 can be configured to include a network management agent that is capable of querying the set of resource servers 108 and computing systems 110 to determine the hardware and software resources. Likewise, the cloud management system 102 can be configured to communicate with external network management systems and/or resources monitoring agents executing on the set of resource servers 108 and computing systems 110 in order to determine the hardware and software resources of the set of resource servers 108 and computing systems 110.

In embodiments, the cloud management system 102 can be configured to identify both the hardware and software resources of the set of resource servers 108 and computing systems 110 and which of those resources are available for use in the cloud. The cloud management system 102 can be configured to identify the hardware resources such as type and amount of processing power, type and amount of memory, type and amount of storage, type and amount of network bandwidth and the like, of the set of resource servers 108 and computing systems 110. Likewise, the cloud management system can be configured to identify the software resources, such as type of OS, application programs, and the like, of the set of resource servers 108 and computing systems 110.

In embodiments, once the computing resources have been identified, the cloud management system 102 can be configured to store an identification of the available resources in an inventory 124 in a repository 126. The repository 126 can be any type of structure configured to store information, such as a database. The repository 126 can be maintained in a computer readable storage device or medium whether local to or remote from the cloud management system 102.

In embodiments, the inventory 124 can be configured to include information that identifies the set of resource servers 108 and computing systems 110 and information identifying the computing resources available. The sets of resource servers 108 and each system in the computing systems 110 can be identified by unique identifiers such as, for instance, Internet Protocol (IP) addresses or other addresses. In the inventory 124, the cloud management system 102 can associate, with each unique identifier, the computing resources available on that computing system.

In embodiments, to instantiate a new set of virtual machines, a requester can transmit an instantiation request to the cloud management system 102. The instantiation request can include the specifications for the set of virtual machines. The specifications can include the particular type of virtual machine they wish to invoke for their intended application. A requester can, for instance, make a request to instantiate a set of virtual machines configured for email, messaging or other applications from the cloud 104 and/or 106. The specifications can also include the type and/or amount of computing resources required. For example, the instantiation request can specify an amount of processing power or input/output (I/O) throughput the user wishes to be available to each instance of the virtual machine or other resources.

In embodiments, the requester's instantiation request can specify a variety of other specifications defining the configuration and operation of the set of virtual machines to be invoked. The instantiation request, for example, can specify a defined period of time for which the instantiated machine or process is needed. The period of time can be, for example, an hour, a day, or other increment of time. In embodiments, the requester's instantiation request can specify the instantiation of a set of virtual machines or processes on a task basis, rather than for a predetermined amount of time. For instance, a requester could request resources until a software update is completed. The requester can also, for instance, specify a service level agreement (SLA) acceptable for their application. One skilled in the art will realize that the requester's request can likewise include combinations of the foregoing exemplary specifications, and others.

In embodiments, the instantiation request can be received and processed by the cloud management system 102, which identifies the type of virtual machine, process, or other resource being requested from the specifications. The cloud management system 102 can then identify the collection of computing resources necessary to instantiate that machine or resource. For example, the set of instantiated virtual machines or other resources can for example comprise virtual transaction servers used to support Web storefronts, or other transaction sites.

In embodiments, the cloud management system 102 can be configured to utilize the specifications from the instantiation request and the inventory 124 of available computing resources to determine which cloud resources to devote to the requester's virtual machines to maximize the computing resources of the clouds 104 and/or 106 and meet the requester's specifications. For example, the cloud management system 102 can select a group of servers in the set of resource servers 108 and/or computing system in the computing systems 110 that match or best match the instantiation request for each component needed to build the virtual machine or other resource.

In embodiments, the cloud management system 102 can maintain a set of "virtual groups," and assign the set of resource servers 108 and computing systems 110 to different "virtual groups". The "virtual groups" can be based on the particular usage (type of virtual machine, application of the virtual machine, function of the virtual machine, and the like) of the members in the groups. For example, the cloud management system 102 can set up a "virtual group" for web servers. The cloud management system 102 can classify the computing resources for the web server "virtual group" based on which computing resources are best suited for web servers. As members of the web server "virtual group" request use of the cloud, the cloud management system 102 can assign the available computing resources classified in the web server "virtual group" to the members. Likewise, the "virtual groups" can be based on the specifications of the computing resources (type and amount of computing resources). For example, the cloud management system 102 can create a "virtual group" for high power computing users. The cloud management system 102 can assign resources to this group that can adequately support computing intensive virtual machines. As members of the high power "virtual group" request use of the cloud, the cloud management system 102 can assign the available computing resources classified in the high power "virtual group" to the members. The cloud management system 102 can maintain the virtual groups in a group record 128 in repository 126.

When the request to instantiate a set of virtual machines or other resources has been received and the necessary resources to build that machine or resource have been identified, the cloud management system 102 can communicate with one or more set of resource servers 108 and/or computing systems 110 to locate resources to supply the required components. The cloud management system 102 can select providers from the diverse set of resource servers 108 and/or computing systems 110 to assemble the various components needed to build the requested set of virtual machines or other resources. It may be noted that in some embodiments, permanent storage such as hard disk arrays may not be included or located within the set of resource servers 108 and the computing resources 110 available to the cloud management system 102, because the set of instantiated virtual machines or other resources may be intended to operate on a purely transient or temporary basis. In embodiments, other hardware, software or other resources not strictly located or hosted in the cloud can be leveraged as needed. For example, other software services that are provided outside of the clouds 104 and 106 and hosted by third parties can be invoked by in-cloud virtual machines. For further example, other non-cloud hardware and/or storage services can be utilized as an extension to the clouds 104 and 106, either on an on-demand or subscribed or decided basis.

With the specification and resources identified, the cloud management system 102 can extract and build the set of virtual machines or other resources on a dynamic or on-demand basis. For example, one set of resource servers 108 or computing systems 110 can respond to an instantiation request for a given quantity of processor cycles with an offer to deliver that computational power immediately and guaranteed for the next hour. A further set of resource servers 108 or computing systems 110 can offer to immediately supply communication bandwidth, for example on a guaranteed minimum or best-efforts basis. In other embodiments, the set of virtual machines or other resources can be built on a batch basis or at a particular future time. For example, a set of resource servers 108 and/or computing systems 110 can respond to a request for instantiation at a programmed time with an offer to deliver the specified quantity of processor cycles within a specific amount of time, such as the next 12 hours.

In embodiments, the cloud management system 102 can then coordinate the integration of the completed group of servers from the set of resource servers 108 and/or computing systems from the computing systems 110, to build and launch the requested set of virtual machines or other resources. The cloud management system 102 can track the combined group of servers selected from the set of resource servers 108, computing systems from the computing systems 110, or other distributed resources that are dynamically or temporarily combined, to produce and manage the requested virtual machine population or other resources.

In embodiments, the cloud management system 102 can then set up and launch the initiation process for the virtual machines, processes, or other resources to be delivered from the cloud. The cloud management system 102 can for instance transmit an instantiation command or instruction to the group of servers in set of resource servers 108 and/or computing system in the computing systems 110. The cloud management system 102 can receive a confirmation message back from each participating server in a set of resource servers 108 and/or computing system in the computing systems 110 indicating a status regarding the provisioning of their respective resources. Various sets of resource servers can confirm, for example, the availability of a dedicated amount of processor cycles, amounts of electronic memory, communications bandwidth, or applications or other software prepared to be served.

In embodiments, the cloud management system 102 can maintain a VM record 130 of each virtual machine instantiated in the clouds 104 and 106. Each virtual machine can be assigned an instantiated machine ID that can be stored in the VM record 130, or other record or image of the instantiated population. Additionally, the cloud management system 102 can store the duration of each virtual machine and the collection of resources utilized by each virtual machine in the VM record 130 and/or inventory 124. The cloud management system 102 can maintain the VM record 130 in the repository 126.

In embodiments, the cloud management system 102 can further store, track and manage a requester's identity and associated set of rights or entitlements to software, hardware, and other resources. Each requester that populates a set of virtual machines in the cloud can have specific rights and resources assigned and made available to them. The cloud management system 102 can track and configure specific actions that a requester can perform, such as provision a set of virtual machines with software applications or other resources, configure a set of virtual machines to desired specifications, submit jobs to the set of virtual machines or other host, manage other requesters of the virtual machines or other resources, and other privileges or actions. The cloud management system 102 can further generate records of the usage of instantiated virtual machines to permit tracking, billing, and auditing of the services consumed by the requester. In embodiments, the cloud management system 102 can for example meter the usage and/or duration of the virtual machines, to generate subscription billing records for a requester that has launched those machines. Other billing or value arrangements are possible.

The cloud management system 102 can configure each virtual machine to be made available to requester and/or users of the one or more networks 120 and/or 122 via a browser interface, or other interface or mechanism. Each instantiated virtual machine can communicate with the cloud management system 102 and the underlying registered set of resource servers 108 and/or computing systems 110 via a standard Web application programming interface (API), or via other calls or interfaces. The instantiated virtual machines can likewise communicate with each other, as well as other sites, servers, locations, and resources available via the Internet or other public or private networks, whether within a given cloud 104 or 106 or between clouds.

It may be noted that while a browser interface or other front-end can be used to view and operate the instantiated virtual machines from a client or terminal, the processing, memory, communications, storage, and other hardware as well as software resources required to be combined to build the virtual machines or other resources are all hosted remotely in the clouds 104 and 106. In embodiments, the virtual machines or other resources may not depend on or require the requester's own on-premise hardware or other resources. In embodiments, a requester can therefore request and instantiate a set of virtual machines or other resources on a purely off-premise basis, for instance to build and launch a virtual storefront or other application.

Because the cloud management system 102 in one regard specifies, builds, operates and manages the virtual machines on a logical level, the requester can request and receive different sets of virtual machines and other resources on a real-time or near real-time basis, without a need to specify or install any particular hardware. The requester's virtual machines, processes, or other resources can be scaled up or down immediately or virtually immediately on an on-demand basis, if desired. In embodiments, the various sets of computing resources that are accessed by the cloud management system 102 to support the virtual machines or processes can change or be substituted, over time. The type and operating characteristics of the virtual machines can nevertheless remain constant or virtually constant, since instances are assembled from abstracted resources that can be selected and maintained from diverse sources based on uniform specifications.

In terms of network management of the virtual machines that have been successfully configured and instantiated, the cloud management system 102 can perform various network management tasks including security, maintenance, and metering for billing or subscription purposes. The cloud management system 102 of a given cloud 104 or 106 can, for example, install or terminate applications or appliances on individual machines. The cloud management system 102 can monitor operating virtual machines to detect any virus or other rogue process on individual machines, and for instance terminate the infected application or virtual machine. The cloud management system 102 can likewise manage the virtual machines or other resources on a collective basis, for instance, to push or deliver a software upgrade to all active virtual machines. Other management processes are possible. Likewise, the cloud management system 102 can be configured to communicate with external network management systems to coordinate the network management functions and processes.

In embodiments, more than one set of virtual machines can be instantiated in a given cloud at the same, overlapping or successive times. The cloud management system 102 can, in such implementations, build, launch and manage multiple sets of virtual machines based on the same or different underlying set of resource servers 108 or computing systems 110, with populations of different sets of virtual machines such as may be requested by different requesters. The cloud management system 102 can institute and enforce security protocols in the clouds 104 and 106 hosting multiple sets of virtual machines. Each of the individual sets of virtual machines can be hosted in a respective partition or sub-cloud of the resources of the clouds 104 and/or 106. The cloud management system 102 of a cloud can for example deploy services specific to isolated or defined sub-clouds, or isolate individual workloads/processes within the cloud to a specific sub-cloud. The subdivision of the clouds 104 and/or 106 into distinct transient sub-clouds or other sub-components which have assured security and isolation features can assist in establishing multiple requesters or a multi-tenant cloud arrangement. In a multiple requesters scenario, each of the multiple requesters can use the cloud platform as a common utility while retaining the assurance that their information is secure from other requesters of the overall cloud system. In further embodiments, sub-clouds can nevertheless be configured to share resources, if desired.

In embodiments, the instantiated virtual machines supported by the cloud 104 can also interact with instantiated virtual machines or processes generated in the ad-hoc cloud 106 or other clouds and vice versa. The cloud management system 102 of clouds 104 and 106 can interface with the cloud management system of other clouds, to coordinate those domains and operate the clouds and/or virtual machines or processes on a combined basis.

As described above, the cloud management system 102 can instantiate and manage the virtual machines instantiated in the clouds 104 and 106. In embodiments, the instantiation and management of virtual machines can be performed by virtual machine (VM) managers separate from the cloud management system 102. The cloud management system 102 can be configured to communicate with the separate VM managers in order to provide the VM managers with the computing resources available in the clouds 104 and 106. The cloud management system 102 can be configured to communicate and cooperate with the VM managers regardless of the virtualization scheme used by the VM managers.

In the foregoing and other embodiments, the requester making an instantiation request or otherwise accessing or utilizing the cloud network can be a person, customer, subscriber, administrator, corporation, organization, or other entity. In embodiments, the requester can be or include another virtual machine, application or process. In further embodiments, multiple requesters and/or entities can share the use of a set of virtual machines or other resources.

Figure 2:
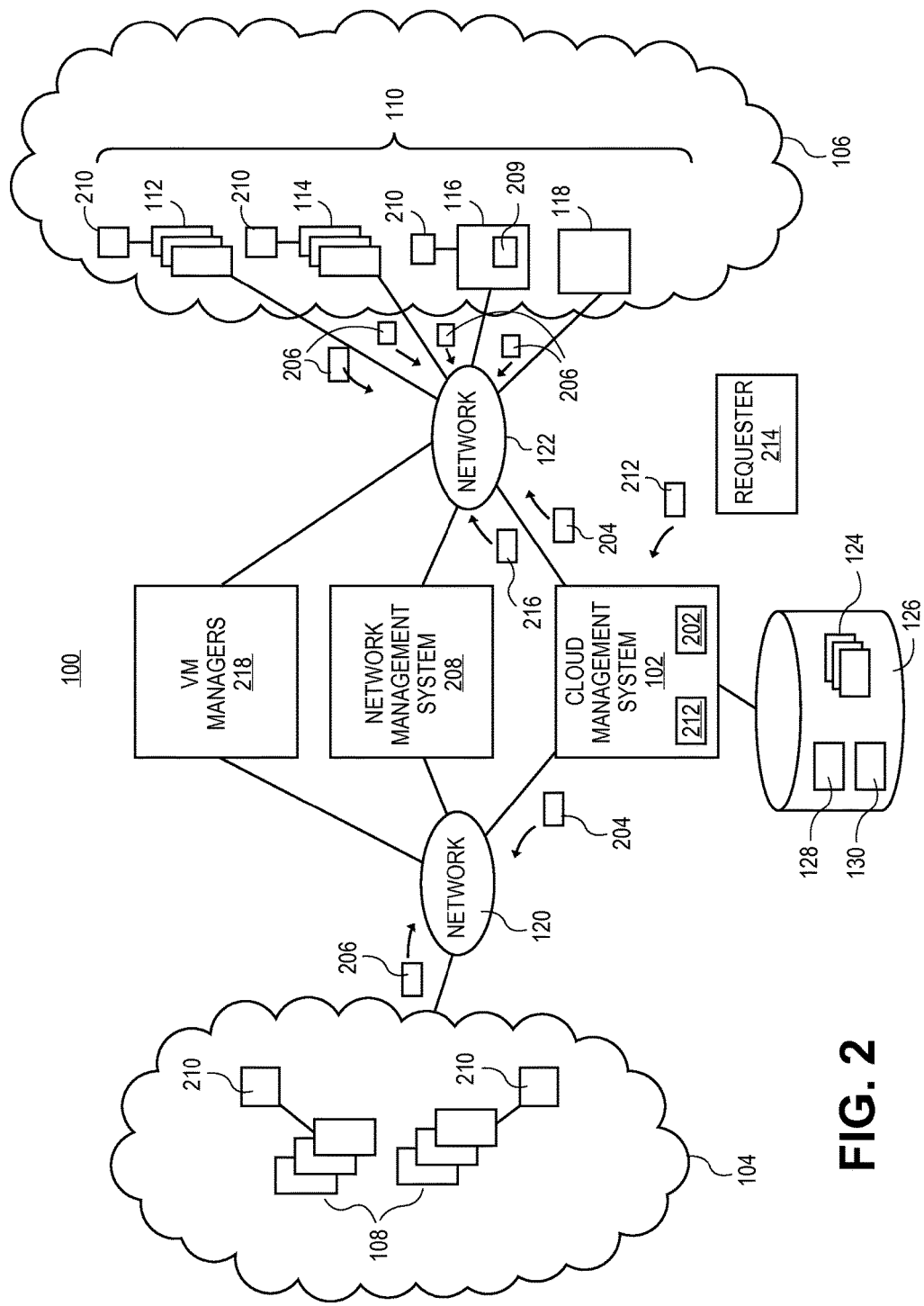
FIG. 2 illustrates the exemplary cloud computing architecture in which a cloud management system can manage a cloud, according to various embodiments.

FIG. 2 further illustrates aspects of the cloud computing environment 100 in which the cloud management system 102 can manage the dedicated cloud 104 and the ad-hoc cloud 106 including providing power management for virtual machine instantiation, according to various embodiments. While FIG. 2 only illustrates the interaction of cloud management system 102 with the dedicated cloud 104 and the ad-hoc cloud 106, one skilled in the art will realize that the cloud management system 102 can manage any number of clouds, for instance, only one of the dedicated cloud 104 and the ad-hoc cloud 106 or other clouds in addition to the dedicated cloud 104 and the ad-hoc cloud 106.

As shown in FIG. 2, the cloud management system 102 can be coupled to a network 120 to communicate with the set of resource servers 108 and coupled to the network 122 to communicate with computing systems 110 to provide management services for the dedicated cloud 104 and the ad-hoc cloud 106. As mentioned above, the dedicated cloud 104 can comprise a set of resource servers 108 configured to deliver computing resources and components needed to instantiate a virtual machine, process, or other resource. The ad-hoc cloud 106 can be composed of a variety of computing resources that may not be dedicated to a cloud but can have available computing resources to contribute to the ad-hoc cloud 106. For example, a corporation or university can have a large number of computing resources that support a variety of process (email, websites, individual user computing, and the like). The corporation or university can utilize the available excess computing resources to support the ad-hoc cloud 106.

In embodiments, as shown in FIG. 2, the ad-hoc cloud 106 can be supported by the computing systems 110 For example, the computing systems 110 can include a variety of systems such as a set of servers 112 and 114 and standalone user computing systems 116 and 118. The computing systems 110 can include hardware resources, such as processors, memory, network hardware, storage devices, and the like, and software resources, such as operating systems (OS), application programs, and the like.

In embodiments, to manage and support the dedicated cloud 104 and the ad-hoc cloud 106, the cloud management system 102 can be configured to identify the computing resources of the set of resources servers 108 and the computing systems 110. The cloud management system 102 can be configured to include a network management agent 202 that is capable of querying the set of resource servers 108 and the computing systems 110 to determine the hardware and software resources. For example, the network management agent 202 can be configured to transmit an identification query 204 to the set of resource servers 108 via the network 120 and to the computing systems 110 via the network 122 and receive a response 206 identifying the computing resources of the set of resource servers 108 and the computing resources of the computing systems 110. Likewise, the network management agent 202 can be configured to directly examine the set of resource servers 108 and the computing systems 110 to determine the computing resources. The network management agent 202 can be configured to include the necessary logic, routines, instruction, and commands to communicate with the set of resource servers 108 and the computing systems 110 in order to identify the computing resources of the set of resource servers 108 and the computing systems 110.

In embodiments, the network management agent 202 can be implemented as a portion of the code for the cloud management system 102. Likewise, the network management agent 202 can be implemented as a separate software tool accessible by the cloud management system 102. The network management agent 202 can be written in a variety of programming languages, such as JAVA, C++, Python code, and the like to accommodate a variety of operating systems, machine architectures, etc. Additionally, the network management agent 202 can be configured to include the appropriate application programming interfaces (APIs) to communicate with and cooperate with other components of the cloud management system 102.

In embodiments, the cloud management system 102 can be configured to communicate with an external network management system 208 in order to determine the computing resources of the set of resource servers 108 and the computing systems 110. The cloud management system 102 can be configured to send a request to the network management system 208 to identify the computing resources. The network management system 208 can be configured to transmit the identification query 204 to the set of resource servers 108 via network 120 and to the computing systems 110 via network 122, to receive a response 206 identifying the computing resources of the set of resource servers 108 and the computing system 110, and to provide the identified computing resources to the cloud management system 102.

In embodiments, the network management system 208 can be any type of network management application or tool to securely communicate with the set of resource servers 108 and the computing systems 110, to monitor the state of the set of resource servers 108 and the computing systems 110, to retrieve and request data from the set of resource servers 108 and the computing systems 110, and to manage and direct the set of resource servers 108 and the computing systems 110. For example, the network management system 208 can be a "FUNC" server as described in U.S. patent application Ser. No. 12/130,424, filed May 30, 2008, entitled "SYSTEMS AND METHODS FOR REMOTE MANAGEMENT OF NETWORKED SYSTEMS USING SECURE MODULAR PLATFORM" (U.S. Patent Application Publication No. 2009/0300180) assigned to Red Hat, Inc., the disclosure of which is incorporated herein, in its entirety, by reference.

In embodiments, in order to aid in identifying the computing resources, the set of resource servers 108 and/or the computing systems 110 can include a resource monitoring agent. For example, as illustrated in FIG. 2, the user computing system 116 can include a resource monitoring agent 209. The resource monitoring agent 209 can be configured to identify the computing resources of the user computing system 116. The resource monitoring agent 209 can provide the identification of the computing resources to the cloud management system 102 and/or network management system 208. The resource monitoring agent 209 can be configured to include the necessary logic, routines, instruction, and commands to communicate with the hardware and software resources of the computing systems 110 in order to identify the computing resources of the set of resource servers 108 and/or the computing systems 110.

In embodiments, the cloud management system 102 and/or network management system 208 can be configured to identify both the hardware and software resources of the set of resource servers 108 and computing systems 110 and which of those resources are available for use in the cloud. The cloud management system 102 can be configured to identify the hardware resources such as type and amount of processing power, type and amount of memory, type and amount of storage, type and amount of network bandwidth and the like, of the set of resource servers 108 and the computing systems 110. Likewise, the cloud management system 102 can be configured to identify the software resources, such as type of OS, application programs, and the like, of the set of resource servers 108 and the computing systems 110.

In embodiments, when identifying the computing resources, the cloud management system 102 and/or network management system 208 can be configured to identify the usage and availability of the set of resource servers 108 and the computing system 110. For example, the computing systems 110 can be supporting other processes outside the ad-hoc cloud 106 and/or virtual machines in the ad-hoc cloud 106, and the set of resource servers 108 can be supporting virtual machines in the dedicated cloud 104. The cloud management system 102 and/or network management system 208 can be configured to identify both the type and total amount of hardware and software resources as well as those currently available for use in the dedicated cloud 104 and the ad-hoc cloud 106.

In embodiments, as illustrated in FIG. 2, one or more of the set of resource 108 and/or one or more of the computing system 110 can be connected to power management systems 210 to control the power supplied to the set of resource servers 108 and the computing systems 110 and to alter the power state of one or more of the set of resource servers 108 and the computing systems 110 (e.g. power cycle). The power management systems 210 can be any type of system to manage the power of the target machines, for example, Integrated Lights Out (ILO) by Hewlett Packard™ Corporation, Dell™ Remote Access Control (DRAC) by Dell Corporation, WTI powerbar by Western Telematics, Inc, and other power system supporting network communications.

In embodiments, when identifying the computing resources of the set of resource servers 108 and the computing systems 110, the cloud management system 102 can be configured to identify the power management systems 210. For example, the cloud management system 102 can be configured to include a request to identify the power management systems 210 in the query 204. The cloud management system 102 can receive the identification of the power management systems 210 in the response 206. The identification of the power management system can include an unique identifier of the power management systems 210, the type of the power management systems 210, and any information necessary to communicate with the power management systems 210 (access information, commands, protocols, instructions, and the like).

In embodiments, the network management system 208 can be configured to identify the power management systems 210 and provide the identification of the power management systems 210 to the cloud management systems 102. Additionally, the identification of the power management systems 210 can be provided to the cloud management system 102 by a third party, such as an administrator of the cloud management system 102.

In embodiments, once the computing resources have been identified, the cloud management system 102 can be configured to store an identification of the available resources in the inventory 124 in the repository 126. The repository 126 can be any type of structure configured to store information, such as a database. The repository 126 can be maintained in a computer readable storage device or medium whether local to or remote from the cloud management system 102.

In embodiments, the inventory 124 can be configured to include information that identifies the set of resource servers 108 and the computing systems 110 and information identifying the computing resources available. The set of resource servers 108 and the computing systems 110 can be identified by unique identifiers such as, for instance, Internet Protocol (IP) addresses or other addresses. For example, each system 112, 114, 116, and 118 can have a unique identifier. In the inventory 124, the cloud management system 102 can associate, with each unique identifier, the computing resources available on that computing system. The inventory 124 can include the type and total amount of hardware and software resources and the type and amount of available hardware and software resources.

In embodiments, the cloud management system 102 can be configured to store the identification of the power management systems 210 in the inventory 124. In the inventory 124, the cloud management system 102 can associate, with each unique identifier of the set of resource servers 108 and the computing systems 110, the identification of the power management systems 210 with which it is associated.

In embodiments, once the computing resources have been identified, the cloud management system 102 can be configured to receive instantiation requests from requesters to instantiate virtual machines in the dedicated cloud 104 and/or the ad-hoc cloud 106. The cloud management system can be configured to receive specifications, in the instantiation requests, of the cloud usage. The specifications can include how the requester plans to use the dedicated cloud 104 and/or the ad hoc cloud 106 (mail server, application server, web server, etc.) and/or specific requirements for the computing resources (amount of processing power, amount of memory, amount of storage, amount of bandwidth, etc.). The cloud management system 102 can be configured to utilize the specifications from the requester and the inventory 124 of available computing resources to determine and allocate which cloud resources to devote to the requester's virtual machines to maximize the computing resources and meet the requester's specifications.

In embodiments, the cloud management system 102 can determine the specific set of resource servers 108 and/or the computing systems 110 and/or the specific computing resources to allocate to the requester's virtual machine. The cloud management system 102 can examine the inventory 124 to determine which of the set of resource servers 108 and/or the computing systems 110 and computing resources are available and meet the specifications of the instantiation request. For instance, the cloud management system can examine the inventory 124 to determine which of the set of resource servers 108 and/or the computing systems 110 and computing resources are available and match or most closely match the specifications of the instantiation request.

In embodiments, once the computing systems and computing resources have been allocated, the cloud management system 102 can be configured to instantiate the virtual machines as specified in the instantiation request, as described above in FIG. 1. The cloud management system 102 can be configured to utilize any type of virtualization scheme to instantiate the virtual machines on the set of resource servers 108 and/or the computing system 110. Likewise, the cloud management system 102 can utilize different type of virtualization schemes on different ones of the set of resource servers 108 and/or the computing systems 110, for instance, depending on which scheme can be supported by a particular one of the set of resource servers 108 and/or computing system 110. The cloud management system 102 can maintain the VM record 130 of each virtual machine instantiated in the dedicated cloud 104 and the ad-hoc cloud 106. Each virtual machine can be assigned an instantiated machine ID that can be stored in the VM record 130. Additionally, the cloud management system 102 can store the duration of each virtual machine and the collection of resources utilized by each virtual machine in the VM record 130 and/or inventory 124. The cloud management system 102 can maintain the VM record 130 in the repository 126.

In embodiments, the cloud management system 102 can be configured to alter the operating state of the set of resource servers 108 and/or the computing systems 110 in order to instantiate the virtual machines. For example, when instantiating a new virtual machine, other existing virtual machines or the virtual machine architecture may need to be re-started in order to instantiate the new virtual machine. Additionally, when instantiating a new virtual machine on a computing system, the operational state of the computing system, itself, may need to be altered in order to instantiate the virtual machine. For example, a particular computing system from the set of resource servers 108 and the computing systems 110 may not currently be supporting any virtual machines. If the cloud management system 102 instantiates a new virtual machine on this particular computing system, the cloud management system 102 can be configured to re-start the particular computing system, for instance, by altering the power state of the particular computing system, in order to initiate the virtual machine architecture and instantiate the virtual machine on the particular computing system.

In embodiments, additionally, the cloud management system 102 can be configured to alter the operating state of the set of resource servers 108 and/or the computing systems 110 for a variety of other reasons. For example, new sets of resource servers 108 and/or the computing systems 110 may need to be added to the dedicated cloud 104 and the ad-hoc cloud 106. In this example, the cloud management system 102 can be configured to alter the power state of the new computing systems in order to add the systems to the dedicated cloud 104 and the ad-hoc cloud 106 and to add new virtual machines to the new computing systems. Likewise, for example, one or more of the set of resource servers 108 and/or the computing systems 110 may be under-utilized (e.g. supporting a fraction of virtual machines possible). In this example, the cloud management system 102 can be configured to migrate the virtual machines from one or more of the under-utilized set of resource servers 108 and/or the under-utilized computing systems 110 and configured to power down the under-utilized set of resource servers 108 and/or the under-utilized computing systems 110.

In embodiments, when instantiating virtual machines on the set of resource servers 108 and the computing systems 110, the cloud management system 102 can be configured to determine if the operational state of the virtual machines, virtual machine architecture, or computing systems need to be altered. To determine if the operational state needs to be altered, the cloud management system 102 can be configured to examine the specifications of the virtual machines and the computing systems to be allocated to determine if the operational state needs to be altered. The cloud management system 102 can be configured to examine the specification of the virtual machines to determine the computing resources to be utilized and configured to examine the inventory 124 and VM record 130 to determine other virtual machines operating on the computing system.

In embodiments, once the determination is made, the cloud management system 102 can be configured to alter the power state of particular one or more of the set of resource servers 108 and the computing systems 110, if necessary. The cloud management system 102 can be configured to communicate with the power management systems 210 of the particular one or more of the set of resource servers 108 and the computing systems 110 to alter the power state. To achieve this, the cloud management system 102 can be configured to include a power management module 212.

In embodiments, the power management module 212 can be configured to communicate with the power management systems 210 of the set of resource servers 108 and the computing systems 110. The power management module 212 can be configured to instruct the power management systems 210 to alter the power state of the set of resource servers 108 and the computing systems 110. The power management module 212 can be configured to generate a command or instruction. The instruction can include access information for the power management systems 210 and the power state alteration to be performed. To determine the access information and the appropriate command or instruction, the power management module 212 can be configured to examine the inventory 124 to determine the identification of the power management systems 210 for the set of resource servers 108 and the computing systems 110 for which the power state will be altered.

In embodiments, the power management module 212 can be configured to form the instruction in a protocol utilized by the particular power management systems 210. For example, the cloud management system 102 can be configured to utilize conventional or proprietary protocols or tools such as IPMI, DRAC, ILO, fence agents and the like. The power management module 212 can be configured to utilize a predetermined protocol or utilize several protocols in order to determine the appropriate protocol. Once generated, the cloud management system 102 can be configured to transmit the instruction to the determined power management systems 210.

In embodiments, the power management module 212 can be implemented as a portion of the code for the cloud management system 102. Likewise, the power management module 212 can be implemented as a separate software tool accessible by the cloud management system 102. Additionally, the power management module 212 can be implemented as a portion of the code for the network management server 208. The power management module 212 can be written in a variety of programming languages, such as JAVA, C++, Python code, and the like to accommodate a variety of operating systems, machine architectures, etc. Additionally, the power management module 212 can be configured to include the appropriate application programming interfaces (APIs) to communicate with and cooperate with other components of the cloud management system 102.

In one example, the cloud management system 102 can receive an instantiation request 212 from a requester 214. The cloud management system 102 can determine that the user computing system 116 and computing resources are available and meet the specifications of the instantiation request 212. When instantiating the virtual machine of the instantiation request 212, the cloud management system 102 can examine the specifications of the instantiation request, the inventory record 124 for the user computing system 116, and the VM record 130 to determine if the virtual architecture needs to be restarted or the operational state of the user computing system 116 needs to be altered.

In this example, the cloud management system 102 can determine that the operational state needs to be altered to instantiate the virtual machine. For instance, the user computing system 116 may not currently be supporting any virtual machine architecture or the computing resources to be allocated to the virtual machine may require the user computing system 116 to be restarted in order for the virtual machine to operate properly. As such, the cloud management system 102 can be configured to retrieve the identification of the power management system 210, associated with the user computing system 116, from the inventory 124. The cloud management system 102 can be configured to instantiate the virtual machine on the user computing system 116 and, then, provide a command 216 to the power management system 210 to alter the power state (e.g. power cycle) of the user computing system 116.

In embodiments, the instantiation and management of virtual machines and the power management described above can be performed by the cloud management system 102. Likewise, the cloud management system 102 can be configured to communicate with one or more VM managers 218 separate from the cloud management system 102. The cloud management system 102 can be configured to communicate with the separate VM managers 218 in order to provide the VM managers 218 with the computing resources allocated to a particular virtual machines and the identification of the power management system 210, if necessary, and the VM managers 218 can be configured to instantiate the virtual machines on the allocated computing resources. The cloud management system 102 can be configured to communicate and cooperate with the VM managers 218 regardless of the virtualization scheme used by the VM managers 218. For example, the VM managers 218 can be a variety of different VM managers supporting virtualization schemes such as Xen, Kernel-based Virtual Machine (KVM), VMware, mainframe ZVM, and the like.

In embodiments, the cloud management system 102 can be configured to update the inventory 124. For example, as computing resources are allocated, the cloud management system can be configured to update the inventory 124 to reflect allocation or de-allocation of computing resources. Additionally, the cloud management system 102 and/or network management system 208 can be configured to periodically query the set of resource servers 108 and the computing system 110 to update the availability of computing resources. The cloud management system 102 can be configured to update the inventory 124 to reflect these updates.

In embodiments, as described above, the cloud management system 102 can alter the operational state of one or more of the set of resource servers 108 and/or the computing systems 110. The cloud management system 102 can be configured to determine whether virtual machines are currently instantiated these set of resource servers 108 and/or the computing systems 110. The cloud management system 102 can be configured to migrate the virtual machines, if necessary, to other of the set of resource servers 108 and/or the computing systems 110 prior to altering the power state of these set of resource servers 108 and/or the computing systems 110. As such, the cloud management system 102 can prevent an interruption of the virtual machines.

Figure 3:
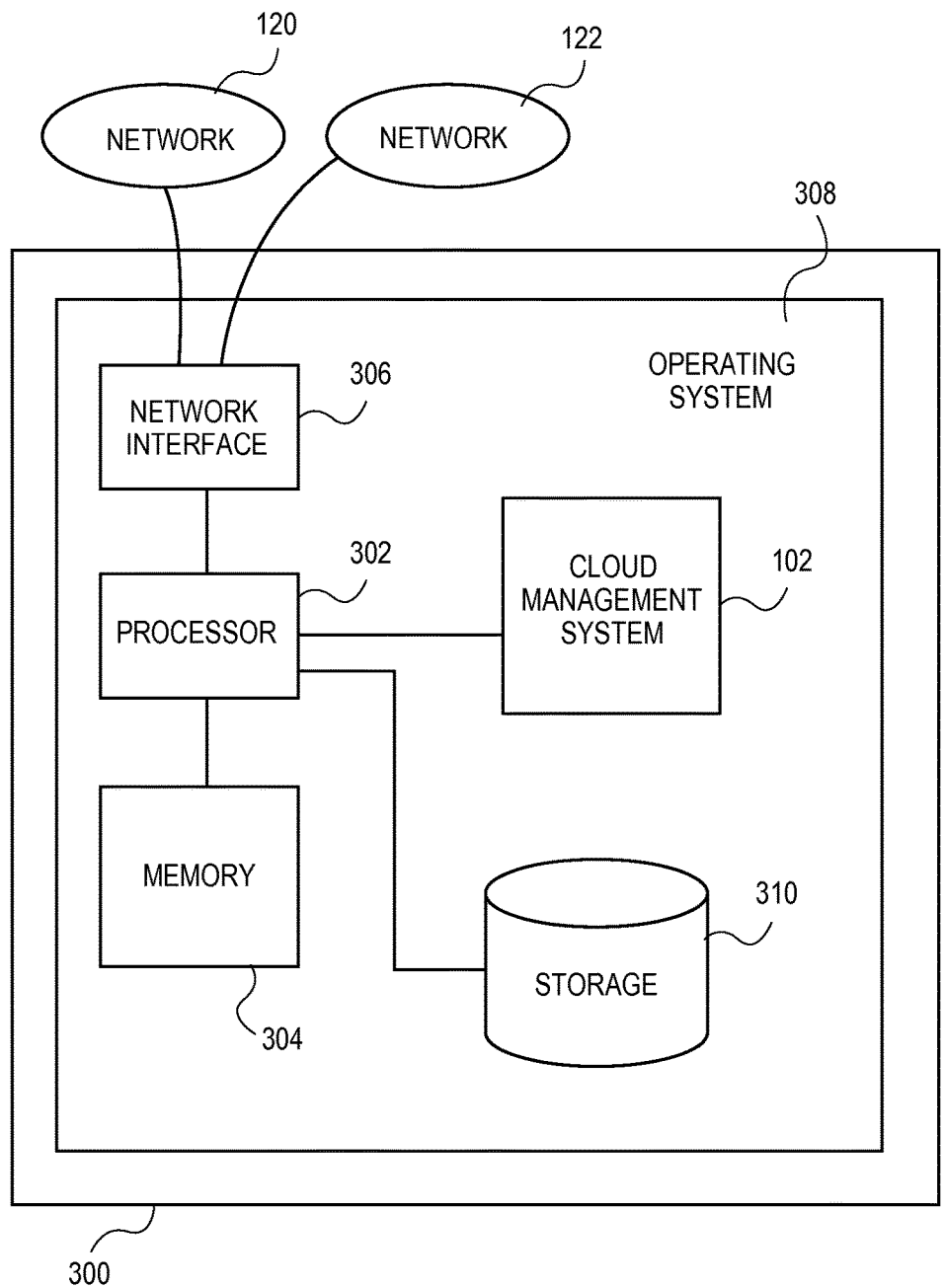
FIG. 3 illustrates an exemplary hardware configuration for a cloud management system, according to various embodiments.

FIG. 3 illustrates an exemplary diagram of hardware and other resources that can be incorporated in a computing system 300 and configured to communicate with the clouds 104 and 106 via one or more networks 120 and 122, according to embodiments. In embodiments as shown, the computing system 300 can comprise a processor 302 communicating with memory 304, such as electronic random access memory, operating under control of or in conjunction with operating system 308. Operating system 308 can be, for example, a distribution of the Linux™ operating system, such as SELinux, the Unix™ operating system, or other open-source or proprietary operating system or platform. Processor 302 also communicates with one or more computer readable storage devices or media 310, such as hard drives, optical storage, and the like, for maintaining the repository 126. Processor 302 further communicates with network interface 306, such as an Ethernet or wireless data connection, which in turn communicates with one or more networks 120 and 122, such as the Internet or other public or private networks.

Processor 302 also communicates with the cloud management system 102, to execute control logic and allow perform the management processes and power management as described above and below. Other configurations of the computing system 300, associated network connections, and other hardware and software resources are possible.

While FIG. 3 illustrates the computing system 300 as a standalone system including a combination of hardware and software, the computing system 300 can include multiple systems operating in cooperation. The cloud management system 102 can be implemented as a software application or program capable of being executed by the computing system 300, as illustrated, or other conventional computer platforms. Likewise, the cloud management system 102 can also be implemented as a software module or program module capable of being incorporated in other software applications and programs. Further, the cloud management system 102 can also be implemented as a software module or program module capable of being incorporated in other management software applications and programs. In any example, the cloud management system 102 can be implemented in any type of conventional proprietary or open-source computer language. When implemented as a software application or program code, the cloud management system 102 can be stored in a computer readable storage medium, such as storage 310, accessible by the computing system 300.

Figure 4:
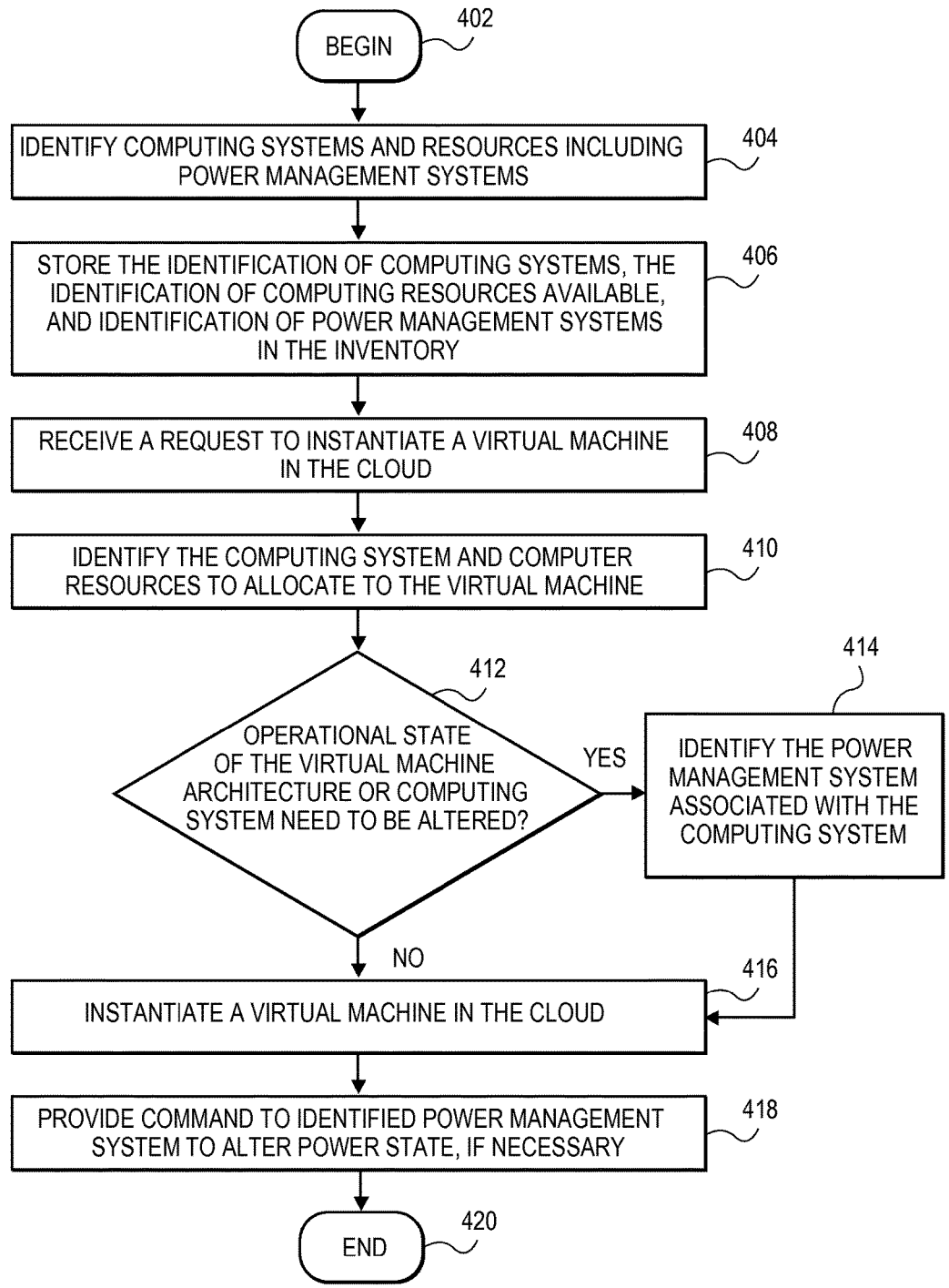
FIG. 4 illustrates a flowchart an exemplary process for managing a cloud including power management, according to various embodiments.

FIG. 4 illustrates a flow diagram flexible management process for a cloud computing architecture, according to embodiments. In 402, processing can begin. In 404, the cloud management system 102 can identify the computing systems and resources for supporting a cloud including power management systems 210 of the computing systems. For example, the cloud management system 102 can query the set of resource servers 108 and the computing systems 110 to identify the type and amount of computing resources and which of these resources are available. Likewise, the cloud management module 102 can communicate with network management systems 208 and/or monitoring agent 209 to determine the computing resources.

In 406, the cloud management system 102 can store the identification computing systems, the identification of computing resources available, and identification of power management systems in the inventory 124. For example, in the inventory 124, the cloud management system 102 can associate, with each unique identifier, the computing resources available on that computing system. The inventory 124 can include the type and total amount of hardware and software resources and the type and amount of available hardware and software resources. The cloud management system 102 can store the identification of the power management systems 210 in the inventory 124. In the inventory 124, the cloud management system 102 can associate, with each unique identifier of the set of resource servers 108 and the computing systems 110, the identification of the power management systems 210 with which it is associated.

In 408, the cloud management system 102 can receive a request to instantiate a virtual machine in the cloud. For example, the cloud management system 102 can receive specifications, in the instantiation requests, of the cloud usage. The specifications can include how the requester plans to use the dedicated cloud 104 and/or ad-hoc cloud 106 (mail server, application server, web server, etc.) and/or specific requirements for the computing resources (amount of processing power, amount of memory, amount of storage, amount of bandwidth, etc.).

In 410, the cloud management system 102 can identify the set of servers 108 and/or the computing systems 110 to allocate to the requester's virtual machine. For example, the cloud management system 102 can determine one or more of the set of servers 108 and/or the computing systems 110 and/or the specific computing resources to allocate to the requester's virtual machine. The cloud management system 102 can examine the inventory 124 to determine which of the set of resource servers 108 and/or the computing systems 110 and computing resources are available and meet the specifications of the instantiation request. For instance, the cloud management system can examine the inventory 124 to determine which of the set of resource servers 108 and/or the computing systems 110 and computing resources are available and match or most closely match the specifications of the instantiation request.

In 412, the cloud management system 102 can determine if the operational state of the virtual machine architecture or computing system needs to be altered. For example, the cloud management system 102 can examine the specifications of the virtual machines and the computing systems to be allocated to determine if the operational state needs to be altered. The cloud management system 102 can examine the specification of the virtual machines to determine the computing resources to be utilized and configured to examine the inventory 124 and VM record 130 to determine other virtual machines operating on the computing system.

If alteration of operation state is required, in 414, the cloud management system 102 can identify the power management system associated with the computing system. For example, the cloud management system 102 can examine the inventory 124 to identify the power management systems 102 associated with the computer systems allocated to the virtual machine.

In 416, the cloud management system 102 can instantiate the virtual machine in the cloud. For example, the cloud management system 102 can directly instantiate the virtual machine on the the selected set of resource servers 108 and/or the computer systems 110 and computer resources, or the computer system can communicate with one or more VM managers 224 to instantiate the virtual machines. The cloud management system 102 can also update the inventory 124 to indicate the allocation of the set of resource servers 108 and/or the computer systems 110 and the computer resources.

In 418, the cloud management system 102 can provide command to identified power management system to alter power state, if necessary. The cloud management system 102 can provide the command directly to the power management systems 210. Likewise, other systems, such as network management systems 202 or VM managers 218, can provide the command to the power management systems 210.

Then, in 420, the process can end, but the process can return to any point and repeat.

Certain embodiments may be performed as a computer application or program. The computer program may exist in a variety of forms both active and inactive. For example, the computer program can exist as software program(s) comprised of program instructions in source code, object code, executable code or other formats; firmware program(s); or hardware description language (HDL) files. Any of the above can be embodied on a computer readable medium, which include computer readable storage devices and media, and signals, in compressed or uncompressed form. Exemplary computer readable storage devices and media include conventional computer system RAM (random access memory), ROM (read-only memory), EPROM (erasable, programmable ROM), EEPROM (electrically erasable, programmable ROM), and magnetic or optical disks or tapes. Exemplary computer readable signals, whether modulated using a carrier or not, are signals that a computer system hosting or running the present teachings can be configured to access, including signals downloaded through the Internet or other networks. Concrete examples of the foregoing include distribution of executable software program(s) of the computer program on a CD-ROM or via Internet download. In a sense, the Internet itself, as an abstract entity, is a computer readable medium. The same is true of computer networks in general.

While the teachings has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method may be performed in a different order than illustrated or simultaneously. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. Those skilled in the art will recognize that these and other variations are possible within the spirit and scope as defined in the following claims and their equivalents.

What is claimed is:

1. A method comprising:
  receiving a request to instantiate a virtual machine, wherein the request specifies a specific period of time for utilization of the virtual machine;
  selecting, by a processor, a computing system from a plurality of computing systems where the virtual machine is to be instantiated based upon the specific period of time specified in the request;

determining, by the processor, that a power state is to be altered, by a power cycle of the computer system, in order to instantiate the virtual machine on the computing system; and altering the power state of the computing system in response to the determining, wherein altering the power state of the computing system comprises performing the power cycle of the computing system.

2. The method of claim 1 further comprising instantiating the virtual machine on the computing system.

3. The method of claim 2 wherein the instantiating of the virtual machine is by a system that is different than the computing system.

4. The method of claim 1 wherein the request comprises a specification of the virtual machine.

5. The method of claim 4 wherein the specification indicates a type of virtual machine.

6. The method of claim 4 wherein, selecting, by the processor, the computing system from the plurality of computing systems where the virtual machine is to be instantiated is based on the specification.

7. The method of claim 1 wherein the altering of the power state comprises providing a command to a power management system.

8. An apparatus comprising:
a network interface; and
a processor, operatively coupled to the network interface, to:
receive, via the network interface, a request to instantiate a virtual machine, wherein the request specifies a specific period of time for utilization of the virtual machine,
select a computing system from a plurality of computing systems where the virtual machine is to be instantiated based upon the specific period of time specified in the request,
determine that a power state of the computing system is to be altered, by a power cycle of the computer system, in order to instantiate the virtual machine, and
alter the power state of the computing system, wherein to alter the power state of the computing system comprises performing the power cycle of the computing system.

9. The apparatus of claim 8 wherein the processor is further to instantiate the virtual machine on a computing system.

10. The apparatus of claim 9 wherein the request comprises a specification of the virtual machine.

11. The apparatus of claim 10 wherein the specification indicates a process to be performed by the virtual machine.

12. The apparatus of claim 10 wherein selection of the computing system from the plurality of computing systems where the virtual machine is to be instantiated is based on the specification.

13. The apparatus of claim 8 wherein to alter the power state the processor is to provide a command to a power management system.

14. A non-transitory computer readable storage medium comprising instructions to cause a processor to:
receive a request to instantiate a virtual machine, wherein the request specifies a specific period of time for utilization of the virtual machine;
select a computing system from a plurality of computing systems where the virtual machine is to be instantiated based upon the specific period of time specified in the request;
determine that a power state is to be altered, by a power cycle of the computer system, in order to instantiate the virtual machine on the computing system; and
alter the power state of the computing system, wherein to alter the power state of the computing system comprises performing the power cycle of the computing system.

15. The non-transitory computer readable storage medium of claim 14 wherein the instructions further cause instantiation of the virtual machine on the computing system.

16. The non-transitory computer readable storage medium of claim 15 wherein the instantiation is by a system that is different than the computing system.

17. The non-transitory computer readable storage medium of claim 14 wherein the request comprises a specification of the virtual machine.

18. The non-transitory computer readable storage medium of claim 17 wherein the specification indicates a computing resource for the virtual machine.

19. The non-transitory computer readable storage medium of claim 17 wherein select the computing system from the plurality of computing systems where the virtual machine is to be instantiated is based on the specification.

20. The non-transitory computer readable storage medium of claim 14 to alter the power state, the processor is to provide a command to a power management system.

* * * * *